United States Patent [19]

Gardano et al.

[11] Patent Number: 5,336,793
[45] Date of Patent: Aug. 9, 1994

[54] PREPARING CARBOXYLIC ACIDS OR ESTERS BY OXIDATIVE CLEAVAGE OF UNSATURATED FATTY ACIDS OR ESTERS

[75] Inventors: Andrea Gardano, Trino; Giampiero Sabarino, Vercelli; Marco Foa', Novara, all of Italy

[73] Assignee: Novamont S.p.A., Milan, Italy

[21] Appl. No.: 988,671

[22] Filed: Dec. 10, 1992

[30] Foreign Application Priority Data

Dec. 11, 1991 [IT] Italy ............... T091A00963

[51] Int. Cl.$^5$ .............. C11C 1/00; C07C 51/25; C07C 67/00
[52] U.S. Cl. .................... 554/138; 554/132; 560/196; 560/265; 562/524; 562/525; 562/590; 562/597
[58] Field of Search ........... 562/524, 525, 590, 597; 560/190, 265; 554/132, 138

[56] References Cited

U.S. PATENT DOCUMENTS 3,855,257 12/1974 Pultinas, Jr. .................... 554/132

FOREIGN PATENT DOCUMENTS 0122804 12/1986 European Pat. Off. .
63-93746 4/1988 Japan .
1324763 7/1973 United Kingdom .

OTHER PUBLICATIONS

*Patent Abstracts of Japan*, vol. 6, No. 63, Apr. 22, 1982 English abstract of Japanese Patent Application 57 004940.
*Chemical Abstracts*, vol. 109, No. 25, Dec. 19, 1988, Columbus, Ohio, US; abstract No. 230298; p. 793; column 1.
Bortolini et al, "Studies in Organic Chemistry," vol. 33, pp. 301–306, (1988).

Primary Examiner—José G. Dees
Assistant Examiner—Vera C. Clarke
Attorney, Agent, or Firm—Bryan Cave

[57] ABSTRACT

A method of preparing carboxylic acids or esters thereof by the oxidative cleavage of unsaturated fatty acids or esters thereof is carried out in a two-phase aqueous-organic system in which the organic phase contains the unsaturated fatty acid and/or the esters thereof and the aqueous phase contains hydrogen peroxide. The oxidative cleavage is carried out in the presence of a catalytic system including a catalyst belonging to the group constituted by tungstic and molybdic acids and alkaline salts thereof, and an onium salt which acts as a phase-transfer agent for the catalyst, and has the formula:

$$(R_2R_3R_4R_5M)^+Y^-$$

in which $R_2$, $R_3$, $R_4$ and $R_5$ represent hydrocarbon groups of which at least one must have more than 10 carbon atoms, M is N or P, and $Y^-$ is an inorganic anion.

9 Claims, No Drawings

PREPARING CARBOXYLIC ACIDS OR ESTERS BY OXIDATIVE CLEAVAGE OF UNSATURATED FATTY ACIDS OR ESTERS

The present invention relates to a method of preparing carboxylic acids or esters thereof by the oxidative cleavage of unsaturated fatty acids or esters thereof in a two-phase aqueous-organic system in which the organic phase contains the unsaturated fatty acid and/or the esters thereof and the aqueous phase contains hydrogen peroxide.

The oxidative cleavage reaction of the most common unsaturated fatty acids and their esters may be represented in the following manner:

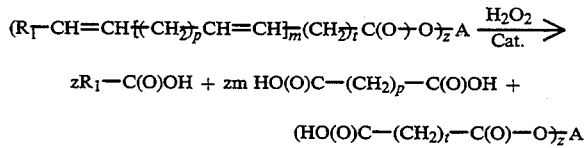

where $p=0-1$, $m=0-2$, $t=0-11$, $z=1-3$, $R_1 =$ H, $C_1$-$C_8$ alkyl or a $CH_3$—$(CH_2)_5$—$CH(OH)$—$CH_2$- radical, if $z=1$, A is H or $C_1$-$C_5$ alkyl, if $z=2-3$, A is the residue of a bivalent or trivalent alcohol.

A method of this type for the oxidative cleavage of unsaturated compounds is described in EP-122804, in which the reaction catalyst used is a compound of the formula $$Q_3XW_4O_{24-2n}$$

where Q represents a cation of an onium salt $(R_6R_7R_8R_9M)^+$ in which M is selected from N, P, As and Sb and $R_6$, $R_7$, $R_8$ and $R_9$ are the same or different and represent hydrogen atoms or hydrocarbon groups having from 20 to 70 carbon atoms in total, X is an atom of P or As and n is a whole number selected from 0, 1 and 2. The method according to EP-122804 also provides for a water immiscible solvent such as, for example, an aromatic or chlorinated hydrocarbon, or the like, to be added to the organic compound to be oxidised.

This method has the disadvantages that the preparation of the catalysts used is complex and difficult and that the solvent used has to be separated from the reaction products and purified for possible reuse.

JP-63093746 describes a method of the type indicated above for the oxidative cleavage of olefins, in which the catalyst used is a compound selected from the group constituted by tungstic acid, molybdic acid and heteropolyacids thereof.

This method has the disadvantage that the conversion yields of the unsaturated compound are very low because it is difficult to transfer the catalyst from the aqueous phase to the organic phase. The rate of transfer of the catalyst, and consequently the conversion yield of the olefin, can be increased with the use of a solvent such as a $C_1$-$C_4$ alcohol, a $C_1$-$C_4$ carboxylic acid, tetrahydrofuran, dioxan, dimethylformamide, etc. which are effective with respect to both polar and non-polar compounds. In this case, however, there is the problem of separating the solvent from the reaction products and purifying it for possible reuse.

The presence of a solvent also makes it difficult to recover and even partially reuse the catalyst and leads to the preferential use of concentrated hydrogen peroxide to prevent the precipitation of the fatty acids and their esters.

GB-1324763 describes a method of oxidising unsaturated compounds in order to produce either the corresponding alcohols or epoxides, or the corresponding acids, as a result of oxidative cleavage. Since the latter takes place, it is indicated that it would be convenient to use a catalytic system constituted by an oxide of osmium or ruthenium and a quaternary ammonium salt which acts as a phase-transfer agent for the oxide, and a more powerful oxidising agent than hydrogen peroxide, such as paraperiodic acid.

Methods of this type are not suitable for application on an industrial scale, however, because of the high cost of the oxidising agent used and because of the toxicity of the catalysts used which means that they have to be disposed of or recovered upon completion of the reaction.

In order to avoid the problems mentioned, the subject of the present invention is a method of the type indicated above, characterised in that the oxidative cleavage is carried out in the presence of a catalytic system including a catalyst belonging to the group constituted by tungstic and molybdic acids and alkaline salts thereof, and an onium salt which acts as a phase-transfer agent for the catalyst, and has the formula:

$$(R_2R_3R_4R_5M)^+Y^-$$

in which $R_2$, $R_3$, $R_4$ and $R_5$ represent hydrocarbon groups of which at least one must have more than 10 carbon atoms, M is N or P, and $Y^-$ is an inorganic anion.

It is particularly surprising that, by virtue of the catalytic system according to the invention, the oxidative cleavage of unsaturated fatty acids or esters thereof can be effected with good yields.

In fact, according to Bertolini et al, in "Studies in Organic Chemistry" vol. 33, pages 301–306 (1988), Elsevier Science Publishers B.V., Amsterdam, in the presence of hydrogen peroxide, tungstic and molybdic acids are transformed into the corresponding peroxo-derivatives. In a protic medium, these derivatives are partially dissociated according to the acid-base equilibrium:

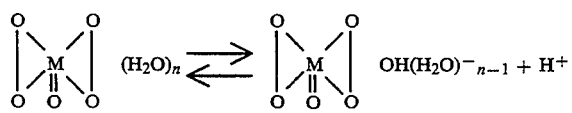

where M=W or Mo.

The neutral and anionic species have different oxidising characteristics; the former is suitable for oxidising systems rich in electrons, such as the olefins, transforming them into epoxides and into the hydrolysis products thereof, the vicinal diols (the first stage of the oxidative cleavage of the double bond), whereas the latter is suitable for oxidising systems with few electrons, such as the alcohols. In this connection, the authors mentioned above use different phase-transfer agents for the transfer from the aqueous phase to the organic phase for the two different oxidising species, the agents being neutral for the non-dissociated species and ionic for the dissociated species.

The ability of the tungstic acid/hydrogen peroxide-/ionic phase-transfer agent catalytic system to bring about the oxidation only of alcohols, particularly vicinal diols, and its inability, on the other hand, to bring about the oxidative cleavage of olefins is also confirmed in EP-122 804, cited above.

In the light of what is reported in the literature, the fact that it is possible to bring about the oxidative cleavage of unsaturated olefinic compounds, such as unsaturated fatty acids and/or esters thereof with industrially acceptable yields, with the use of a catalytic system including, according to the invention, a solely ionic phase-transfer agent, is thus wholly unpredictable.

The method according to the invention has the advantage that the catalysts and phase-transfer agents used are compounds which can easily be obtained commercially so that it is not necessary to synthesise and purify them directly.

Moreover, the method of the invention ensures optimal reactivity of the catalytic system and enables easy separation of the catalyst used.

In preferred embodiments of the invention, the quantity of the catalyst used is between 0.5 and 10% by weight with reference to the quantity of fatty acid or ester to be oxidised, and the quantity of the onium salt used is between 0.1 and 5% by weight, again with reference to the quantity of fatty acid or ester to be oxidised.

Examples of onium salts used to carry out the method of the invention are methyltrioctylammonium chloride, dimethyldioctadecylammonium chloride, dimethyldihexadecylammonium chloride, hexadecyltrimethylammonium chloride, octadecyltrimethylammonium chloride, hexadecyltributylphosphonium chloride, and the like.

Also in preferred embodiments of the invention, a molar excess of between 10 and 100% of hydrogen peroxide, with reference to the stoichiometric quantity necessary to effect the oxidative cleavage, which corresponds to 4 moles of hydrogen peroxide per mole of unsaturated bond, is used. The concentration of the hydrogen peroxide in the aqueous solution is preferably between 20 and 70% (weight/volume) and even more preferably between 35 and 60% (weight/volume).

The oxidative cleavage reaction according to the invention is preferably carried out at a temperature of between 60° and 150° C. Above 105° C. it is necessary to operate under pressure.

Examples of substrates to be subjected to oxidative cleavage are oleic, ricinoleic, linoleic, linolenic, arachidonic, erucic, palmitoleic, 9-dodecylenic, 9-decylenic and stillingic acids and mixtures thereof, the corresponding esters of mono- and polyvalent alcohols, and mixtures thereof.

The method of the invention may be carried out, for example, by loading the compound to be oxidised, the aqueous solution of hydrogen peroxide, the catalyst and the phase-transfer agent into a reactor all at once, and heating the mixture to the predetermined reaction temperature with vigorous stirring. Alternatively, the compound to be oxidised and/or the aqueous solution of hydrogen peroxide may be added gradually over a period of time.

The reaction time may vary between 1 and 24 hours according to the experimental conditions selected (the quantity of catalyst, the quantity and concentration of the hydrogen peroxide, the temperature, and the like).

The progress of the reaction is determined by checking the composition of the reaction mixture periodically by suitable analytical methods such as, for example, gas chromatography of the gaseous or liquid phase.

Upon completion of the reaction, the stirring is stopped and the organic phase is separated from the aqueous phase. When the latter has been suitably separated from the organic products it contains, it may be recycled, after it has been concentrated, since it contains some of the catalyst used. The reaction products are separated with the use of conventional techniques. In particular, the esters of the mono- and dicarboxylic acids are separated by fractional distillation under vacuum and the carboxylic acids may be obtained by the hydrolysis of the corresponding esters, or directly from the reaction mixture by making use of their different solubilities in water and their different boiling points.

Further advantages and characteristics of the method of the invention will become clear from Examples 1–5 below which are not intended to limit the scope of the present invention. Example 6 is comparative and demonstrates the increased yield obtainable by means of a method according to the invention in comparison with a method in which a catalyst such as tungstic acid is used in the absence of a phase-transfer agent.

EXAMPLE 1

A 500 cm$^3$ flask with a mechanical stirrer, a thermometer and a reflux condenser was loaded with 51 g of crude methyl oleate (purity=80%) containing 9.9% of linoleic acid methyl ester, 100 cm$^3$ of 35% $H_2O_2$, 0.5 g of $H_2WO_4$ and 1.2 g of Arquad 2HT (registered trade mark, produced by the company AKZO and consisting of quantities of 75% and 25%, respectively, of dimethyldioctadecyl chloride and dimethyldihexadecylammonium chloride.

The mixture was heated to 100°–104° C. with stirring and was kept at that temperature for 6 h. Upon completion of the test, the mixture was cooled to ambient temperature and diluted with ethyl ether. The organic layer was separated from the aqueous phase. Analysis showed that 76% of the tungsten used was present in the aqueous phase. The organic phase was evaporated and 200 cm$^3$ of $CH_3OH$ containing 1 cm$^3$ of concentrated $H_2SO_4$ were added to the residue. The mixture was refluxed for 6 h and the methanol was then evaporated. The residue was taken up with ethyl ether and washed with water to eliminate the free acidity. After the ether had been evaporated, a residue of 60 g was obtained and was subjected to fractional distillation under a vacuum of 3 mm of Hg. 18.9 g of methyl pelargonate (yield=79.7%) and 24.6 of methyl azelate (yield=77%) were obtained.

EXAMPLE 2

The following reagents were added to the apparatus used in Example 1: 100 g of sunflower oil (saponification index=162.8 mg KOH/g; oleic acid content=81% of the fatty acids present, linoleic acid content=8.4% of the fatty acids present), 200 cm$^3$ of 35% $H_2O_2$, 1.0 g of $H_2WO_4$ and 1.0 g of Arquad 2HT (registered trade mark).

The mixture was heated to 105° C. for 8 h with stirring. Upon completion of the reaction, the mixture was cooled to ambient temperature and diluted with ethyl ether.

The organic phase was separated from the aqueous phase and evaporated. 350 cm$^3$ of $CH_3OH$ containing 5 cm³ of concentrated H₂SO₄ was added to the residue. The mixture was refluxed for 8 h. The methanol was then evaporated and the residue was taken up with ethyl ether and washed copiously with water. After the ether had been evaporated, the residue (105.3 g) was subjected to fractional distillation under a vacuum of 3 mm of Hg. 29.8 g of methyl pelargonate (yield=73.5%) and 40.5 g of methyl azelate (yield=72.5%) were obtained.

EXAMPLE 3

The following reagents were added to the apparatus used in Example 1: 100 g of crude oleic acid (purity=80%, linoleic acid content=9.9%), 167 cm³ of 35% H₂O₂, 2.0 g of H₂WO₄ and 2.0 g of Arquad 2HT (registered trade mark). The mixture was heated to 100°–104° C. with stirring and was kept at that temperature for 6 h.

Upon completion of the test, the aqueous phase was separated and the organic phase was subjected to continuous extraction with water at 95° C.

The aqueous phases were cooled to 5° C. and then filtered to produce 41.6 g of azelaic acid. The crystallisation waters, which were usable in the next test, contained 1.75 g of azelaic acid. The overall yield of this acid was 72.3%.

The residual organic phase was subjected to fractional distillation yielding 34.9 g of pelargonic acid (yield=77.9%).

EXAMPLE 4

The apparatus described in Example 3 was loaded with the same quantities of reagents except that 2.0 g of Arquad 2HT were replaced by 2.0 g of tricaprylylmethylammonium chloride. 35.8 g of pelargonic acid (total yield 79.9%) and 45.1 g of azelaic acid (total yield 75.2%) were obtained by the method described above.

EXAMPLE 5

The apparatus used in Example 3 was loaded with the following reagents: 103 g of crude oleic acid (purity=80%, linoleic acid content=9.9%), 2.0 g of H₂WO₄ and 2.0 g of Arquad 2HT. 105 cm³ of 60% H₂O₂ were gradually added to the mixture which was stirred continuously and kept at a temperature of between 100° and 109° C. for a period of about 5 hours. Treatment was carried out as described in Example 3 and 39.8 g of pelargonic acid (total yield 86%) and 46.8 g of azelaic acid (total yield 76% ) were obtained.

EXAMPLE 6 (COMPARATIVE)

The following reagents were added to the apparatus of Example 1: 48 g of crude oleic acid (purity=80%, linoleic acid content=9.9%), 100 cm³ of 35% H₂O₂ and 4.8 g of H₂WO₄.

The mixture was heated to 100°–104° C. with stirring and was kept at that temperature for 24 h. The reaction mixture was treated as described in Example 1 to give a yield of methyl pelargonate and methyl azelate of 8–9%.

We claim:

1. A method for the preparation of carboxylic acids or esters thereof, the method comprising the oxidative cleavage of an unsaturated fatty acid or ester thereof in a two-phase aqueous-organic system, the organic phase containing the unsaturated fatty acid or ester thereof and the aqueous phase containing hydrogen peroxide, wherein the oxidative cleavage is carried out in the presence of a catalytic system, said catalytic system comprising (a) a catalyst selected from the group consisting of tungstic acid, molybdic acid, alkaline salts of tungstic acid and alkaline salts of molybdic acid, and (b) an onium salt which acts as a phase-transfer agent for the catalyst, the onium salt having the formula:

$$(R_2R_3R_4R_5M)^+ Y^-$$

in which $R_2$, $R_3$, $R_4$ and $R_5$ represent hydrocarbon groups of which at least one must have more than 10 carbon atoms, M is N or P, and $Y^-$ is an inorganic anion.

2. A method according to claim 1, wherein the quantity of the catalyst is between 0.5 and 10% by weight with reference to the quantity of the unsaturated fatty acid or ester thereof to be oxidized.

3. A method according to claim 1, wherein the quantity of the onium salt used is between 0.1 and 5% by weight with reference to the quantity of the unsaturated fatty acid or ester thereof to be oxidized.

4. A method according to claim 1, wherein the onium salt used is selected from the group consisting of methyltrioctylammonium chloride, dimethyldioctadecylammonium chloride, dimethyldihexadecylammonium chloride, hexadecyltrimethylammonium chloride, octadecyltrimethylammonium chloride and hexadecyltributylphosphonium chloride.

5. A method according to claim 1, wherein the hydrogen peroxide is present in a molar excess of between 10 and 100% with reference to the stoichiometric quantity necessary to effect the oxidative cleavage.

6. A method of claim 5, wherein the hydrogen peroxide is present in the aqueous phase in a concentration of between 20 and 70%, weight/volume.

7. A method of claim 6, wherein the hydrogen peroxide is present in the aqueous phase in a concentration of between 35 and 60%, weight/volume.

8. A method of claim 1, wherein the cleavage is carried out at a temperature of between 60° and 150° C.

9. A method according to claim 1, wherein the unsaturated fatty acid or ester thereof is selected from the group consisting of oleic, ricinoleic, linoleic, linolenic, arachidonic, erucic, palmitoleic, 9-dodecylenic, 9-decylenic and stillingic acid, mixtures thereof, the corresponding esters of mono- or polyvalent alcohol, and mixtures thereof.

* * * * *